United States Patent [19]

Southard

[11] Patent Number: 5,565,407
[45] Date of Patent: Oct. 15, 1996

[54] BIOLOGICALLY ACTIVE AGENT ENCAPSULATED IN BIODEGRADABLE STARCH/POLYMER MATRICES

[75] Inventor: Marylee Z. Southard, Lawrence, Kans.

[73] Assignee: University of Kansas Center for Research, Inc., Lawrence, Kans.

[21] Appl. No.: 359,008

[22] Filed: Dec. 19, 1994

Related U.S. Application Data

[63] Continuation-in-part of Ser. No. 173,097, Dec. 27, 1993, abandoned.

[51] Int. Cl.$^6$ .......................... A01N 25/10; A01N 25/26
[52] U.S. Cl. .......................... 504/116; 504/234; 424/488; 424/493; 424/497; 424/499; 514/122; 514/778; 514/788; 514/965; 71/DIG. 1
[58] Field of Search .......................... 504/116, 234; 71/DIG. 1; 424/488, 499, 497, 493; 514/778, 788, 965, 122

[56] References Cited

U.S. PATENT DOCUMENTS

| | | | |
|---|---|---|---|
| 4,282,207 | 8/1981 | Young et al. | 424/78 |
| 4,911,952 | 3/1990 | Doane et al. | 427/213.31 |
| 5,082,655 | 1/1992 | Snipes et al. | 424/386 |
| 5,256,711 | 10/1993 | Tokiwa et al. | 525/411 |

FOREIGN PATENT DOCUMENTS

| | | |
|---|---|---|
| 0126827 | 12/1984 | European Pat. Off. . |
| WO9107949 | 6/1991 | WIPO . |
| WO9215285 | 9/1992 | WIPO . |
| WO9307859 | 4/1993 | WIPO . |

OTHER PUBLICATIONS

Vollner et al.; IAEA–SM–297/27, pp. 113–122, 1991.
Chem. Ab., 1572, Director of Special Libraries & Information Center–1993.
Chem. Ab., 107:60979p; Wittwer 1987.
Lenaerts et al.; Journal of Controlled Release, 15 (1991) 39–46.
Ramsay et al.; Appl. Environ. Microbiol., vol. 59, No. 4, Apr. 1993, pp. 1242–1245.
Eith et al.; Drug Development and Industrial Pharmacy, 12(11–13), 2113–2126 (1986).
Voris et al.; Pesticide Formulations: Innovations and Developments; Root Growth Inhibition, pp. 223–240 1990.
ACS Ab. 1992, vol. 204, No. 155.
ACS Ab. 1990, vol. 200, No. 170.

*Primary Examiner*—S. Mark Clardy
*Attorney, Agent, or Firm*—Hovey, Williams, Timmons & Collins

[57] ABSTRACT

Improved release-extending compositions are provided for encapsulation of bioactive agents which exhibit reduced release rates of the bioactive agent from the composition matrix when compared with conventional encapsulated formulations, most preferably employed in agricultural applications for insect and weed control. The compositions of the invention from about 25–75 wt. % (non-active ingredient basis) native, undenatured starch, from about 25–75 wt. % (non-active ingredient basis) biodegradable synthetic polymer, and from about 1–40 wt. % bioactive agent.

18 Claims, 10 Drawing Sheets

Fig. 17. (Loading: 20 ppm in 90:10 starch/PEG matrix)

Fig. 16. (Loading: 20 ppm in 75:25 starch/PEG matrix)

Fig. 19.

Fig. 18.   (Loading: 10 ppm in 90:10 starch/PEG matrix)

Fig. 20.

BIOLOGICALLY ACTIVE AGENT ENCAPSULATED IN BIODEGRADABLE STARCH/POLYMER MATRICES

This application is a continuation-in-part application under 37 CFR 1.62 of prior application Ser. No. 08/173,097, abandoned, filed on Dec. 27, 1993.

BACKGROUND OF THE INVENTION

1. Field of the Invention.

The present invention is broadly concerned with improved, release-extending compositions for encapsulation of bioactive agents, which compositions exhibit reduced release rates of bioactive agents when compared with conventional encapsulated formulations. More particularly, the compositions of the invention include respective quantities of native, undenatured starch and biodegradable synthetic polymer wherein the polymer coats at least a portion of the starch surface area, with a quantity of bioactive agent interspersed within the admixture.

2. Description of the Prior Art.

The controlled release of any bioactive ingredient, whether pesticide, drug or fertilizer, facilitates safe and effective use. Controlled-release technology focuses on the need for the application of an active compound to a system to accomplish a specific purpose while avoiding ineffective underdosing or toxicity from overdosing. Ideally, the active agent is released at a controlled rate and maintains its concentration in the system within optimum limits for an extended period. Thus, much less of the active ingredient is required for the same period of activity than in conventional methods of administration.

When applied by conventional methods, pesticides are invariably subject to leaching, evaporation, and degradation (photolytic, hydrolytic, and microbial), all of which remove the active ingredients from their site of action before they can perform their function. In most cases following application, the rate of degradation follows first order kinetics. See, Lewis and Cowsar, "Principles of Controlled Release Pesticides", H. B. Scher, Ed., Controlled Release Pesticides (ACS Symp. Ser. 53), *Am. Chem. Soc.*, Washington, DC, p11, 1977. Thus, if $M_e$ is the minimum effective level, $M_0$ the amount of agent to be released during conventional methods of administration, and $k_r$ the release rate constant, then $t_e$, the time during which an effective level of active agent is present after a single application, would be:

$$t_e = \frac{1}{k_r} \ln \frac{M_o}{M_e}$$

It follows from the above equation that, to increase the duration of the effective action of a conventionally applied pesticide, the application of an exponentially greater quantity of the active agent is required. On the other hand, if the minimum effective level of active ingredient required is supplied by means of a controlled-release formulation, then the optimum amount of the active agent would be released and the duration of action would be:

$$t_e = \frac{M_\infty - M_e}{K_d * M_e}$$

where $K_d$ is the rate constant for active agent delivery from a controlled-release device and $M_\infty$ is the total amount of active agent encapsulated in the device. See, Zeoli and Kydomieus, "An Overview of Controlled Release Technology", *Bioengineering Aspects*, p63, 1983.

In the past, however, attempts to affect the controlled release of bioactive ingredients from controlled-release devices have suffered several disadvantages. In agricultural applications employing pure starch as the release device, the release rate of the pesticide is often too rapid because of biological attack of the starch matrix following field application. As a result, dangerously high levels of pesticide can develop in rain run-off from fields, which can lead to contamination of water sources used for human consumption. In some cases, the pesticide formulation will float and merely contributes to ever higher pesticide levels in the rain fun-off from fields.

The cost of processing the controlled-release device or composition is often substantially higher than that associated with standard release formulations. By way of example, injection-molding techniques to processing unmodified starch with other unknown excipients into capsules (CAPILL™) includes processing steps involving cycle time, screw speed, and critical temperature control, together with expensive injection-molding equipment. Various approaches to the controlled release of chemical agents by means of a starch-based encapsulating material had been disclosed previously. Some of these approaches have involved the use of chemical crosslinking reactions and chemical bonding between the encapsulating materials. In U.S. Pat. No. 4,911,952, Doane discloses a system for encapsulation of chemical biological agents in a cooked starch system without the use of chemical crosslinking reagents. The system encapsulates the agent exclusively with starch which has been blended into an aqueous dispersion at an elevated temperature to permit reassociation with amylose molecules upon cooling of the starch/agent mixture. The result is that the reassociation forms a starch matrix entrapping discontinuous domains of the agent within the starch interstices of the reassociated starch chains. This system, however, suffers a disadvantage in that when exposed to aerobic environments or to organisms such as algae and fungi, typically found in the soil and water in agricultural settings, the reassociated starch matrix may undergo rapid degradation resulting in an undesirably high rate of release of the encapsulated agent. In agricultural settings, rapid release rates of the agents can lead to soil and ground water contamination problems.

In U.S. Pat. No. 4,282,207, Young et al. disclose a method and composition for the controlled release of pesticides by using a mixture comprising (a) a carbinol-containing organic polymer, (b) a crosslinking agent for the polymer consisting essentially of a hydrolyzable silane or organopolysiloxane containing hydrolyzable silane groups or partial hydrolyzates thereof, and (c) a pesticide. The method and composition calls for the crosslinking reaction between hydroxyl groups associated with the carbinol-containing organic polymer and either the hydrolyzable silane groups.

Some devices used to produce controlled release of bioactive agents create an adverse environmental impact, not only because of the presence of the device itself in the environment, but also because of the presence of device degradation products in the environment resulting from heat, hydrolysis, oxidation, solar radiation, and biological degradation.

Accordingly, the requirements for a successful slow-release composition for the encapsulation of bioactive ingredients are exceedingly stringent, with the most troublesome difficulty being excessively rapid release of the active ingredient following application.

The slow-release device itself, together with the degradation products of the release device (following heat, hydrolysis, oxidation, solar radiation, and biological degradation), can create an adverse environmental impact.

SUMMARY OF THE INVENTION

The present invention overcomes the problems outlined above, and provides improved slow-release compositions for the encapsulation of bioactive ingredients to extend the period of time during which bioactive ingredients are released from the composition. The invention is predicated upon the discovery that improved slow-release compositions can be formulated through use of a mixture of native, undenatured starch and synthetic biodegradable polymers wherein the polymer coats at least a portion of the starch surface area, with a quantity of bioactive ingredient interspersed within the mixture. The method and composition of the instant invention provides such a slow-release composition for the encapsulation of bioactive ingredients without the use of chemical crosslinking reagents.

Advantageously, the composition should include from about 25 to 75 wt. % (non-active portion) undenatured starch, and more preferably from about 50 to 65 wt. % thereof.

In more detail, the compositions employ poly(ecaprolactone) (a polyester) and polyethylene glycol, either singly or in combination, as the synthetic polymers. The compositions should contain from about 25 to 75% by weight (non-active portion) synthetic polymer, and more preferably from about 35 to 50% by weight thereof. Other possible compounds which may be substituted for the synthetic polymers (e.g., poly caprolactone and polyethylene glycol) are those listed in 21 CFR § 172 (Food Additives Permitted for Direct Addition to Food for Human Consumption); 21 CFR § 181 (Prior Sanctioned Food Ingredients); 21 CFR § 182 (Substances Generally Recognized as Safe); 21 CFR § 184 (Direct Food Substances Affirmed as Generally Recognized as Safe); and the FDA list of "Inactive Ingredients for Approved Prescription Drug Products", *New Eng. J. Med.*, 309, 439 (1983). The synthetic polymers employed in the inventive compositions are those which advantageously undergo reduction to carbon dioxide and water after composition application on a field in a particular growing season, but before the next growing season.

The compositions can be formulated with any bioactive ingredient, and when the compositions are put to agricultural use, the most preferred active ingredients are atrazine and trifluran. Advantageously, the composition should include from about 1 to 40% by weight atrazine. It is also possible to formulate compositions wherein the active ingredient is malathion for agricultural uses such as insect control within silos used for grain storage. The compositions may also be formulated with bioactive agents for use as medications in humans or animals.

In practice, the ingredients of the compositions are interspersed to create a mixture; and other optional ingredients can be provided which do not detract from the use properties of the compositions.

The compositions of the invention are preferably formulated for giving the compositions a reduced release rate of the active ingredient from the composition matrix following application, as compared with comparative release rates from prior art devices.

The compositions of the invention can provide the following improved properties over conventional formulations (e.g., pure starch/atrazine manufactured by the USDA) according to the invention as taught by U.S. Pat. No. 4,911,952, to Doane et al., including the following:

(a) The compositions and processing methods affect the release rate of the incorporated agent, and therefore can be used to achieve the desired release period.

(b) Reduced concentration of active ingredient in rainfall run-off from soil areas is achieved compared to conventional formulation.

(c) The enzymatic attack on starch in the composition matrix is delayed or prolonged by using excipients such as biodegradable synthetic polymers.

(d) Although the compositions exhibit diffusional release at early times in a biological environment, the presence of synthetic polymer in the compositions lowers the apparent diffusivity of the active agent through the matrix and thereby increases the lifetime of such a composition.

(e) Conventional starch/active agent formulations (e.g., USDA pure starch/atrazine formulations) release active agent faster because of enzymatic attack on starch which, in the inventive compositions, is restricted by limited accessibility due to the synthetic polymer. (Eventually the polymeric components of the inventive matrix are degraded (PCL and PEG by fungi and starch by amylase enzymes), but at a much slower rate than the active ingredient release rate.)

DETAILED DESCRIPTION OF THE PREFERRED EMBODIMENT

The following examples set forth preferred compositions and techniques for formulation thereof, as well as best results demonstrating the reduced release rate of active agent from the compositions.

The active ingredient used in the starch/polymer compositions was "Aatrex" (90 wt. % atrazine ("Aatrex" 90 wt. % active agent, Ciba-Geigy). The active ingredient used in the USDA composition was technical grade atrazine. The polymers used in the compositions were poly($\epsilon$-caprolactone) (PCL) (molecular weight—about 7800 gm/gm-mole) and polyethylene glycol (PEG) (molecular weight—about 8000 gm/gm-mole) and were obtained from Aldrich Chemical Co. The starch used in the starch/polymer compositions of the examples was native, undenatured ungelatinized cornstarch and was obtained from National Starch and Chemical Company and is about 70% by weight amylose and 30% by weight amylopectin. Ungelatinized starch is used in the formulation of the instant invention to avoid a number of problems associated with the use of gelatinized, or partially gelatinized starch. In particular, gelatinized starch is not as durable when used in a slow release composition in that the active agent will be released at undesirably high release rates due to rapid degradation of the starch from biological and aerobic attack. In addition, the use of ungelatinized starch avoids the processing problems associated with the handling of sticky gelatinized starch, which in formulation represents an extra and expensive processing step. The pure starch/atrazine composition (i.e. compositions without polymer) was obtained from the USDA (USDA Experimental Station, Peoria, Ill) and included 11.3 wt. % atrazine. (The formulation of atrazine in the pure starch/atrazine composition, as used in examples, is described in Carr, M. E., Wing, R. E. and Doane, W. M., "Encapsulation of Atrazine in Starch by Twin Screw Extrusion", *Cereal Chem.*, 68(3) pp 262–266, 1992, and is also described in U.S. Pat. No. 4,911,952 to Doane et al.)

The malathion used in the starch/polymer compositions was "Fyafanon" (96 wt. % active agent, Cheminova). The polymer used in the composition as polyethylene glycol (PEG) (molecular weight —about 1000 gm/gm-mole, M. P. about 38° C.) and was obtained from Aldrich Chemical Co. The starch used in the starch/polymer compositions of the example was native undenatured wheat starch and was obtained from the Grain Science Department of Kansas State University.

The starch/polymer compositions used in the malathion example were made by the following process. The formulation mixing process was carried out in a Brabender mixer equipped with a mixing bowl (25 g or 50 g capacity) and a set of twin screws which subjected the contents to high shear. The speed of mixing was set at 40 rev/s. The equipment was set up in a "dry room" where the air humidity was controlled to less than 3%. The temperature of the mixing bowl was set at 43° C. Once a steady temperature was reached, starch and malathion were added to the mixing bowl and the mixing was started. The malathion, a liquid, was added in an appropriate amount to the starch, so as to achieve the desired loading (measured in weight percent). Immediately after, the PEG was added and the contents were mixed for about 10–15 minutes at the above room temperature, so as to effectively create a starch/polymer matrix. In this example, the mixture was allowed to mix for 15 minutes which provided enough time to obtain a homogenous blend. Mixing was then stopped and the blend was removed from the mixing bowl and allowed to cool. This blend was then ground in a fine powder.

For the example, two starch/polymer compositions were formulated—a composition containing 75% by weight pure starch and 25% by weight PEG and a composition containing 90% by weight pure starch and 10% by weight PEG.

The starch/polymer compositions used in the examples were made by the following process. The formulation mixing process was carried out in a Brabender mixer equipped with a mixing bowl (25 g or 50 g capacity) and a set of twin screws which subjected the contents to high shear. The speed of mixing was set at 40 rev/s. The equipment was set up in a "dry room" where the air humidity was controlled to less than 3%. The temperature of the mixing bowl was set at 80° C. Once a steady temperature was reached, starch was added to the mixing bowl and mixing was started. The starch was allowed to reach the set temperature after which the PCL or PEG or both were added. During the mixing of starch and synthetic polymer as set forth above, the temperature is preferably maintained between 85° to 175° C. for about 10 to 15 minutes to effectively create a starch/polymer matrix. The temperature may be advantageously maintained at any temperature less than the degradation temperature of the active ingredient, provided that the temperature is sufficiently high to melt at least a portion of the polymer so that the polymer effectively mixes with and coats a portion of the starch granules. The selection of an appropriate polymer and its molecular weight range may be advantageously based on the desired processing temperature, which processing temperature is governed by the degradation temperature of the selected active ingredient. In particular, a lower polymer melting temperature may be obtained by selecting a polymer with a shorter chain length and molecular weight. In this example, the mixture was allowed to mix for 15 minutes which provided enough time to obtain a homogeneous blend. Powdered atrazine was added to the blend to achieve the desired loading (measure in weight percent) and allowed to mix for another 15 minutes. Mixing was then stopped and the blend was removed from the mixing bowl and allowed to cool. The blend was then either compression molded into slabs (0.5 cm wide by 0.2 cm thick) in a Carver Press at a temperature of 80° C. and a force of 1 ton, or if granular material was desired, the blend was ground and sieved. The slab temperature was cooled to room temperature before removing from the mold. For particle-size studies, the slabs were then either cut into smaller pieces or ground and sieved depending on the experiments for which they were designed.

For the examples, two starch/polymer compositions were formulated to create a formulation matrix of the instant invention—a composition containing 50% by weight (non-active basis) pure starch and 50% by weight (non-active basis) PCL ("50:50 starch/PCL") and a composition containing 50% by weight (non-active basis) pure starch, 25% by weight (non-active basis) PCL, and 25% by weight (non-active basis) PEG ("50:25:25 starch/PCL/PEG").

Example 1 (Lab Flume Tests)

Example 1 is a laboratory flume test demonstrating that the release rates of atrazine from the polymer/starch compositions of the instant invention into flume run-off are substantially less than the release rates of atrazine from both unencapsulated solid atrazine and the pure starch/atrazine composition.

Example 1 presents data from experiments which simulated field run-off conditions and was carried out in a horizontal plexiglass flume (16 feet×0.5 feet). The flume included a flow development section (10 feet long) followed by a bed (six feet long, 1 inch deep) of glass beads. Glass beads (1 mm O.D., bulk porosity: 0.4) were used as a surrogate medium for soil to eliminate soil-formulation interactions such as atrazine-soil adsorption and enzymatically induced metabolic degradation of the formulation matrix. Thus, the use of glass beads instead of soil shows the purely diffusive-convective transport properties of atrazine from the formulations into the bed, and ultimately into bed run-off water.

Short-term and long-term laboratory flume experiments using glass beads were conducted using the following compositions: (1) unencapsulated solid atrazine; (2) a pure starch/atrazine blend with 11.3 wt. % active agent); (3) a 50:50 starch/PCL blend with 25 wt. % active agent; and (4) a 50:25:25 starch/PCL/PEG blend with 25 wt. % active agent. All encapsulated formulations were granular having a −18+30 mesh sieve size range. The glass beads were thoroughly washed with tetrahydrofuran and water between consecutive experiments.

For both short-term and long-term laboratory flume experiments, the flume glass bead bed was saturated with water before the application of the compositions. Just enough water was used to wet the glass beads completely. For each experiment, 0.27 gm of atrazine (active agent basis) of each composition was spread over a small surface area (7 cm×15.2 cm) at the end of the bed. To simulate over-land flow, water was passed over the bed from a constant head tank. A flow rate of about 205 cc/s (3.25 gpm) and a depth of about 2.7 cm were established resulting in a flow velocity of about 5 cm/s (considered to be representative of water run-off flow conditions in fields following a heavy rainfall). A sieve (50 mesh size) was placed at the outlet of the flume to catch solid run-off to test for compositions that float. Samples were collected from the run-off effluent stream at different times and were analyzed to determine the atrazine concentration. The effluent stream was collection in a storage tank.

Short-term laboratory flume runs (3 hour duration) were conducted in triplicate for each composition experiment. The short-term laboratory flume runs provided a measure of the magnitude of error in experimentation and tested reproducibility of the results.

Long-term laboratory flume experiments (24 hour duration) were conducted to test slow release rate performance of the compositions and to test the extent to which the compositions float. The atrazine mass flow rate for any given time was calculated by multiplying the atrazine concentration in samples taken from the effluent stream by the volumetric flow rate of the effluent stream. The mass flow rate of atrazine in the effluent was plotted as a function of time and the cumulative atrazine mass released in the effluent was determined by summing the area under the atrazine mass flow rate versus time plot (using the trapezoidal rule).

For both the short-term and long-term laboratory experiments, the atrazine content in effluent samples were measured by immunoassay procedures using kits acquired from Ohmicron (Newton, Pa.) (a procedure found to be sensitive to atrazine concentrations in the range of 1–10 ppb).

Table 1 below presents data showing solid composition entrainment in the effluent for the different compositions of Example 1.

TABLE 1

SOLID ENTRAINMENT FOR DIFFERENT FORMULATIONS

| COMPOSITION | WEIGHT OF SOLID ENTRAINMENT (Active Agent Basis) (g) | TIME AT WHICH ENTRAINMENT STOPPED (s) |
|---|---|---|
| Unencapsulated Solid Atrazine | 0.0014 | 7 |
| Pure starch/ atrazine (11.3 wt % loaded) | 0.0169 | 30 |
| 50:50 Starch/PCL (25 wt % loaded) | 0 | N.A. |
| 50:25:25 Starch/PCL/ PEG (25 wt % loaded) | 0 | N.A. |

The data of Table 1 show that when compositions of the invention are used, substantial reductions in the amount of solid composition that floats in rain run-off can be obtained when compared with both the unencapsulated solid atrazine and pure starch/atrazine formulations.

Figure 1:
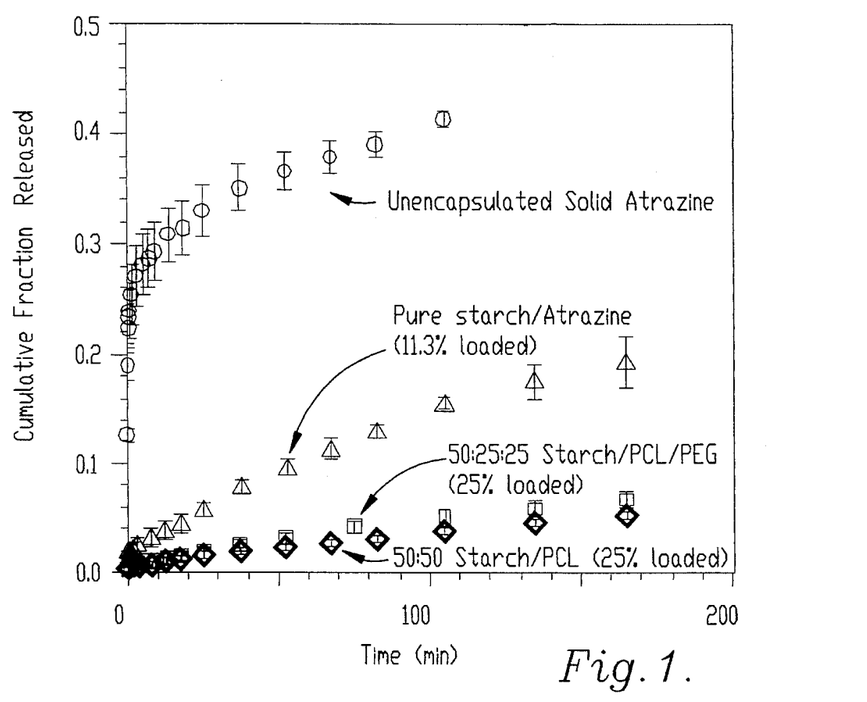
FIG. 1 is a graph showing a comparison between formulations for short times in the laboratory flume experiments.

FIG. 1 is a plot comparing the release rates of compositions tested in the short-term experiments of Example 1. FIG. 1 shows the cumulative fraction of atrazine released as a function of time for each formulation (cumulative fraction of atrazine released=$(M_t)/(M_o)$, where $M_t$=total mass of atrazine released up to time t (active agent basis); and $M_o$=total mass atrazine applied (active agent basis).

The data points appearing in FIG. 1 represent the average of triplicate runs and the error bars denote the standard deviation between the points for a given set. FIG. 1 shows that the release rate of atrazine from the pure starch/atrazine composition is slower than for that of the unencapsulated solid atrazine. Further, the atrazine release rates associated with the polymer/starch compositions of the invention are substantially lower than that associated with the pure starch/ atrazine composition.

Figure 2:
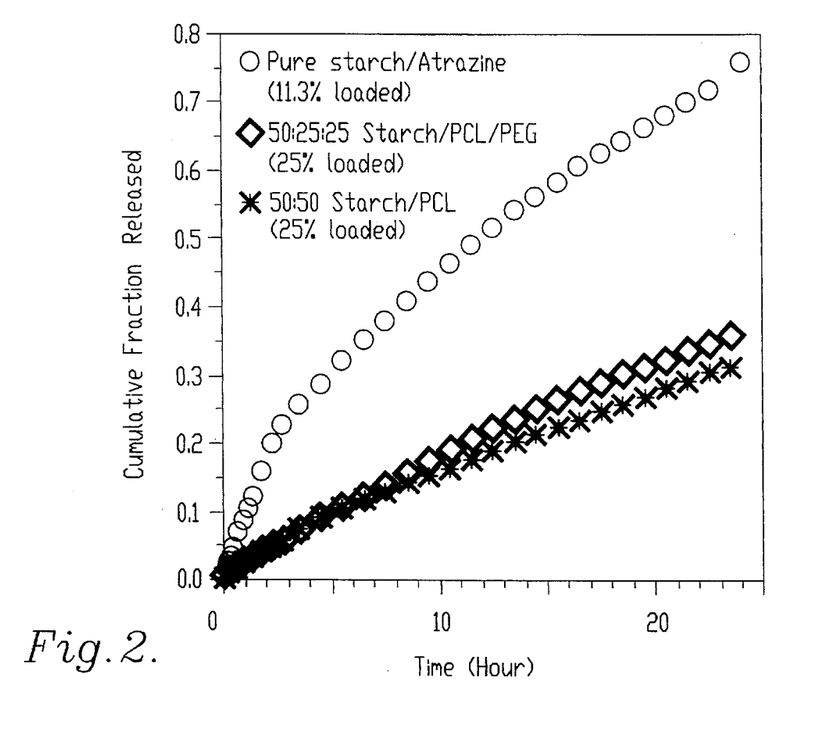
FIG. 2 is a graph showing a comparison between formulations for long times in the laboratory flume experiments.

FIG. 2 is a comparison between atrazine release rates associated with the compositions for long-term experiments of Example 1. FIG. 2 shows that the atrazine release rate from the pure starch/atrazine formulation is about three times faster than that associated with the starch/polymer based compositions of the invention. Although the presence of PEG in the starch/polymer formulation increases the rate of release of atrazine, the increase is not significant.

A mass balance experiment was performed to insure that the experimental results were not significantly affected by unaccounted losses during the experiments of Example 1. The mass balance experiment comprised a test run using 0.272 gm of unencapsulated solid atrazine using the heavy rainfall simulation procedures described above for the short-term experiment. At the end of the experimental run, the effluent bed glass beads were washed in methanol. The methanol was collected and its atrazine content measured. The results of the mass balance experiment appear in Table 2. This experiment shows that the methodology of the flume glass bead bed experimental procedure was sound.

TABLE 2

MASS BALANCE CLOSURE FOR FLUME EXPERIMENTS

| SOURCE | MASS OF ATRAZINE RECOVERED (g) | PERCENTAGE OF LOADED ATRAZINE |
| --- | --- | --- |
| Effluent | 0.109 | 40 |
| Solid Run-off | 0.0014 | 0.5 |
| Beads Wash Solution | 0.174 | 64 |
| (approximate due to some evaporation of methanol while cleaning) | | |
| Total | 0.2844 | 104.5 |

Example 2 (Short-Term Soil Flume Experiment)

This example was designed to simulate a severe field test (immediate heavy rain following field application) for all atrazine compositions to demonstrate the advantage of the starch/polymer formulations of the invention. In terms of atrazine in the run-off, this example sets up a worst-case scenario for the unencapsulated solid atrazine because insufficient time is provided for a) adsorption of atrazine into soil and subsequent migration, and b) enzymatic attack on the starch component (of compositions employing starch) to enhance atrazine release. This example shows that the release rate of active agent from the starch/polymer compositions of the instant invention into field run-off water associated with heavy rains (immediately after application) is significantly lower than that associated with both the unencapsulated solid atrazine and the pure starch/atrazine formulation.

EXPERIMENTAL SET-UP FOR EXAMPLE 2

Figure 3:
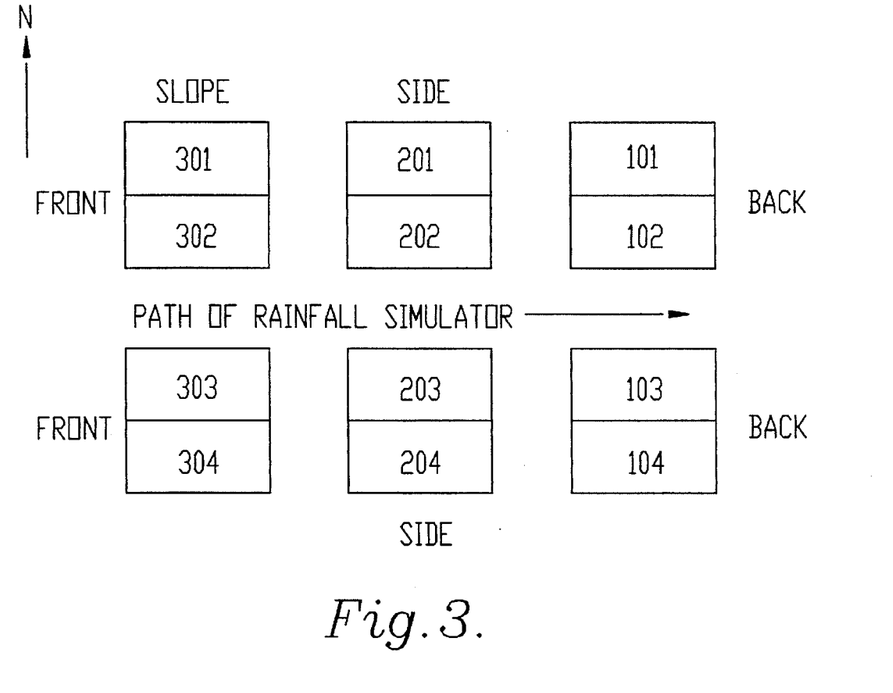
FIG. 3 is a test plot arrangement of the short-term soil flume experiment.

The experiments associated with Example 2 were performed on test plots shown in FIG. 3.

The test plots are located at Silver Lake Experimental Field Site, located northwest of Topeka, Kans. The test plot soil type was clayey-loam. Each test plot had dimensions of 5 ft.×30 ft. A triangular shaped aluminum flume was located at the front of each plot. Aluminum flashing was positioned along the back and sides. The height of the flashing above ground level was about 8 cm (3.15 in.) to isolate and route run-off from each plot towards the front for collection of run-off.

The release rate and characteristics of four compositions were tested all at one time. Each test was performed three times. The composition applied to a plot in each group was varied randomly (ie., the first test run, plot 301, may have had unencapsulated solid atrazine, while in the second test run, unencapsulated solid atrazine may have been applied to plot 204.) For each test, the formulations applied had the following active agent loading:

(1) 2.787 gm unencapsulated solid atrazine;
(2) 12.836 gm pure starch/atrazine at 11.3 wt. % loading (active agent basis);
(3) 12.836 gm 50:50 starch/PCL at 22.5 wt. % loading (active agent basis); and
(4) 12.836 gm 50:25:25 starch/PCL/PEG at 22.5 wt. % loading (active agent basis).

A rainfall simulator was used to simulate rainfall at 2.5 inches per hour. The simulator moved between plots along the path shown in FIG. 3.

The formulations were surface applied to the plots without any incorporation into the soil. Formulations (1) through (4) above were applied to plots 301–304 (i.e., for the first test run, plot 301 may have had unencapsulated solid atrazine applied, while in the second test, unencapsulated solid atrazine may have been applied to plot 204.) This procedure was followed for the 100 and 200 series plots as the rainfall simulator was moved east for use on each series of plots.

EXPERIMENTAL PROCEDURE

The rainfall simulator began at the 300 series plots and moved in the direction of the 100 series plots. Initial samples of plot run-off were taken as the run-off began. Effluent samples were collected in buckets from the flumes for 15 seconds at the following times after run-off began: 1, 5, 12, 20, 40, 50, 60 and 65 minutes. Water samples for triazine analysis were taken at time 0, 2, 8, 15, 25, 35, 45, 55, 60 and 65 minutes.

Atrazine undergoes degradation in soil and the class of compounds which includes atrazine and its degradation products is known as triazines. (See, C. Adams, *Occurrence and Control of Atrazine Degradation Products in Kansas Drinking Water Supply*, Ph. D Dissertation, 1991). Thus, water samples were analyzed for triazine concentration so that degradated atrazine would not be overlooked.

The triazine mass flow rate for any given time was calculated by multiplying the triazine concentration in samples by the volumetric flow rate. The triazine mass flow rate was plotted as a function of time and the cumulative triazine mass released in the run-off was determined by summing the area under the triazine flow rate versus time plot (using the trapezoidal rule).

RESULTS

Figure 4:
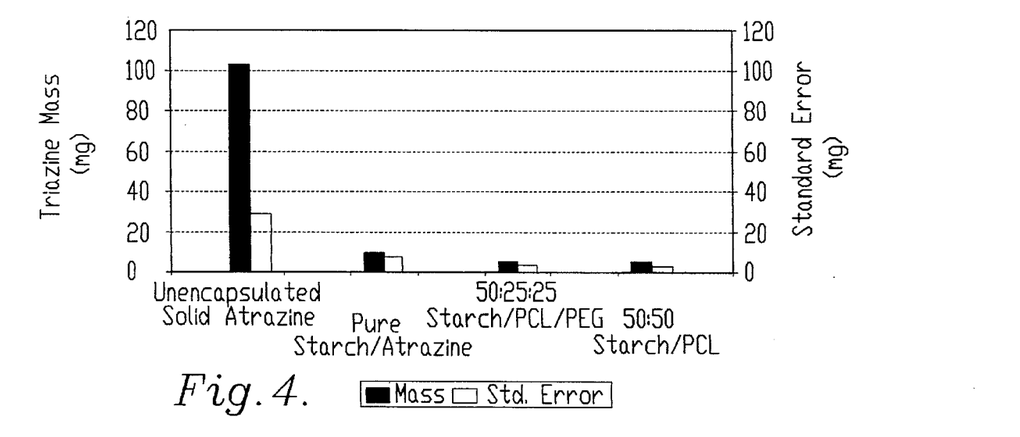
FIG. 4 is a graph showing the mass and standard error of triazine in short-term soil flume run-off.

The total mass of triazine was averaged and standard error of the mean due to experimental variance was calculated for each composition. The total mass in the run-off for each composition appears in FIG. 4 and Table 3 below.

TABLE 3

MASS AND STANDARD ERROR OF TRIAZINE IN SHORT-TERM SOIL FLUME RUN-OFF

| FORMULATIONS | MASS OF TRIAZINE (mg) | STANDARD ERROR (mg) |
| --- | --- | --- |
| Unencapsulated Solid Atrazine | 102.9 | 28.6 |
| Pure Starch/Atrazine | 8.6 | 6.7 |
| 50:50 Starch/PCL | 5.3 | 3.4 |
| 50:25:25 Starch/PCL/PEG | 5.3 | 2.9 |

Example 3 (Long-Term Field Study)

This example was designed to simulate heavy rains on a long-term basis. In terms of atrazine in the run-off, this example sets up a worst-case scenario for the pure starch/atrazine composition because sufficient time is provided for enzymatic attack on the starch component of the composition (and subsequent release of atrazine) and also because unencapsulated solid atrazine has had time to bind to the soil. The data presented in Example 3 demonstrate that the starch/polymer formulations of the invention significantly reduce the release rate of active agent from the composition during heavy rains on a long-term basis with attendant decrease of free agent in field run-off.

EXPERIMENTAL SET-UP

Figure 5:
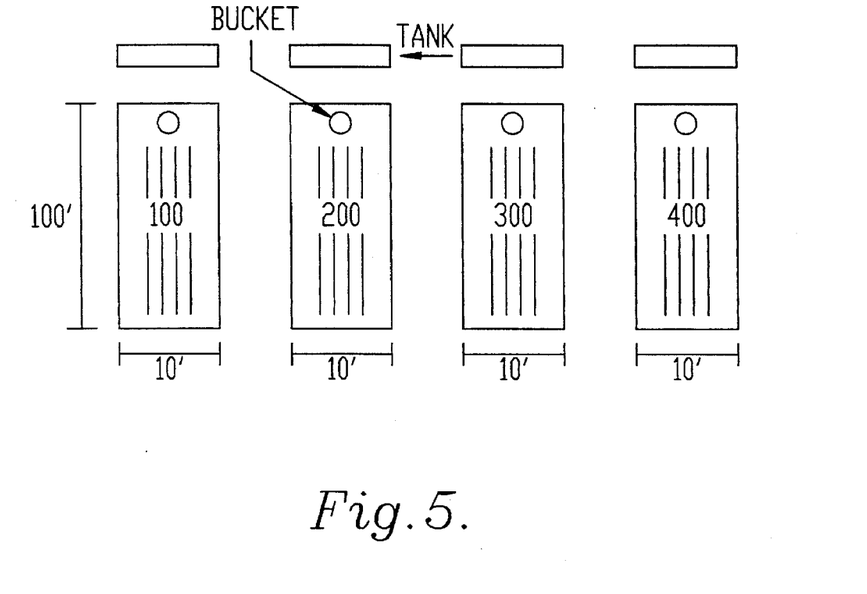
FIG. 5 are long-term field study plots.

The formulations used in this example are the same as those used in Example 2. The formulations were applied to plots arranged as shown in FIG. 5. Only one formulation was applied to each plot. The slope of the plot was about 0.2%.

Each plot was separated by a distance of 5 ft. to prevent cross-contamination. A sunken trough was positioned at field level at the down-sloped end of each test plot to catch the run-off. After each rainfall (each rainfall considered a separate event) a pump in the bottom of each trough allowed collected run-off to be pumped through a hose to a large feed trough where the total volume could be measured. Each plot was bordered by a dirt berm to prevent run-off from escaping.

For each event the triazine mass in the run-off collected in the troughs was measured by first stirring the trough contents, then sampling the contents for triazine concentration (by immunoassay). The total triazine mass in the run-off was calculated by multiplying the triazine concentration by the volume of water in the trough.

EXPERIMENTAL PROCEDURE

The formulation applied to each test plot is listed below:
(1) 18.58 gm unencapsulated solid atrazine;
(2) 185.8 gm pure starch/atrazine at 11% loading (active agent);
(3) 82.57 gm 50:50 starch/PCL at 22.5% loading (active agent); and
(4) 82.5 gm 50:25:25 starch/PCL/PEG at 22.5% loading (active agent).

The unencapsulated solid atrazine was mixed with water according to manufacturer's directions ("Aatrex"-Ciba-Geigy) and the atrazine/water solution was applied by tractor drawn boom sprayers. The other compositions (which are granular) were applied to the plots by hand. The compositions were incorporated into the soil on all four plots to a depth of 2 to 4 inches. The herbicide Alachlor was applied (2 lbs/acre) to control grass weed growth in the plots and all plots were fertilized with nitrogen. Four rows of field corn were planted on each plot immediately after fertilizer and herbicide were applied.

RESULTS

Figure 6:
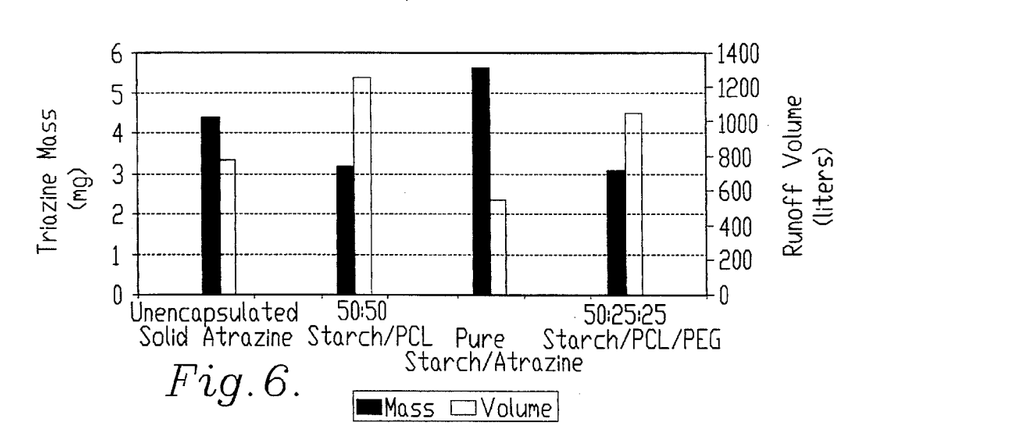
FIG. 6 is a graph showing the total triazine mass and run-off volume from the long-term field study.

The data indicate that the formulations of the inventions (formulations 3 and 4) significantly reduce the concentration of atrazine and atrazine degradation products in the run-off. Table 4 and FIG. 6 present the results of the samples taken during the long-term field study of Example 3.

TABLE 4

TOTAL TRIAZINE MASS AND RUN-OFF
VOLUME FROM LONG-TERM FIELD STUDY

| FORMULATIONS | MASS (mg) | VOLUME (Liters) |
| --- | --- | --- |
| Unencapsulated Solid Atrazine | 4.37 | 774 |
| Pure Starch/Atrazine | 5.6 | 569 |
| 50:50 Starch/PCL | 3.16 | 1255 |
| 50:25:25 Starch/PCL/PEG | 3.08 | 1053 |

It is noted that a disparity existed between the volumes collected from each plot as reported in Table 4. That is, one skilled in the art would expect that volumes collected would be about the same since each plot was subjected to the same rainfall conditions. The disparity arose because of technical difficulties experienced with the equipment used to pump run-off collected from each plot. It will be appreciated, however, that while less than all the run-off was collected from the plots to which unencapsulated solid atrazine and pure starch/atrazine formulations were applied, the data are nonetheless valid to demonstrate the effectiveness of the formulations of the invention. That is, referring to Table 4, the total mass of atrazine in the run-off from plots to which unencapsulated solid atrazine and pure starch/atrazine formulations were applied was substantially greater than the total mass of atrazine in the run-off from the plots to which the formulations of the invention were applied.

Figure 7:
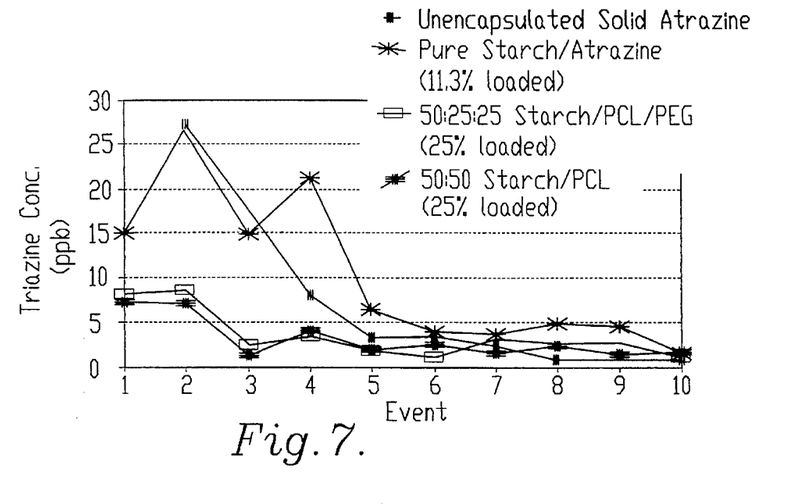
FIG. 7 is a graph showing the triazine concentration in the long-term field study run-off.

FIG. 7 below presents graphically the amount of triazine concentration in each composition for each sample event.

The release of atrazine from the starch/polymer formulations was studied through a series of bottle tests. The bottle tests show that: (1) the difference in atrazine release rates from the polymer/starch formulations of the instant invention is not significant; (2) the release rates of atrazine from 50:50 starch/PCL formulations with 10 wt. % and 30 wt. % initial atrazine loadings do not vary significantly; (3) the type of starch used (amylose/amylopectin) does not have a significant effect on the atrazine release rate; and (4) increasing formulation particle size surface area dramatically increases the rate of atrazine release.

Figure 8:
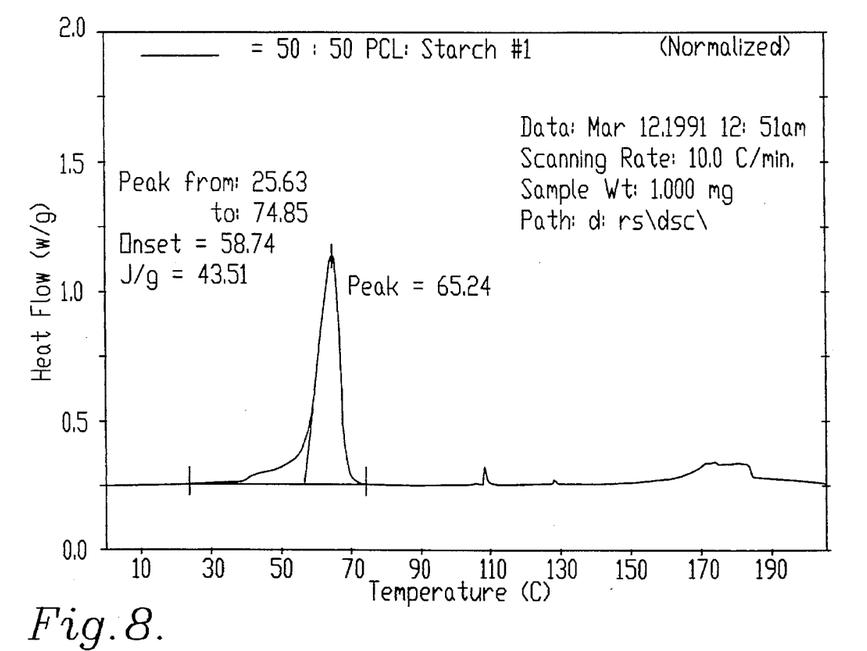
FIG. 8 is a differential scanning calorimetry (DSC) for a 50—50 starch-PCL blend after five minutes of mixing.
Figure 9:
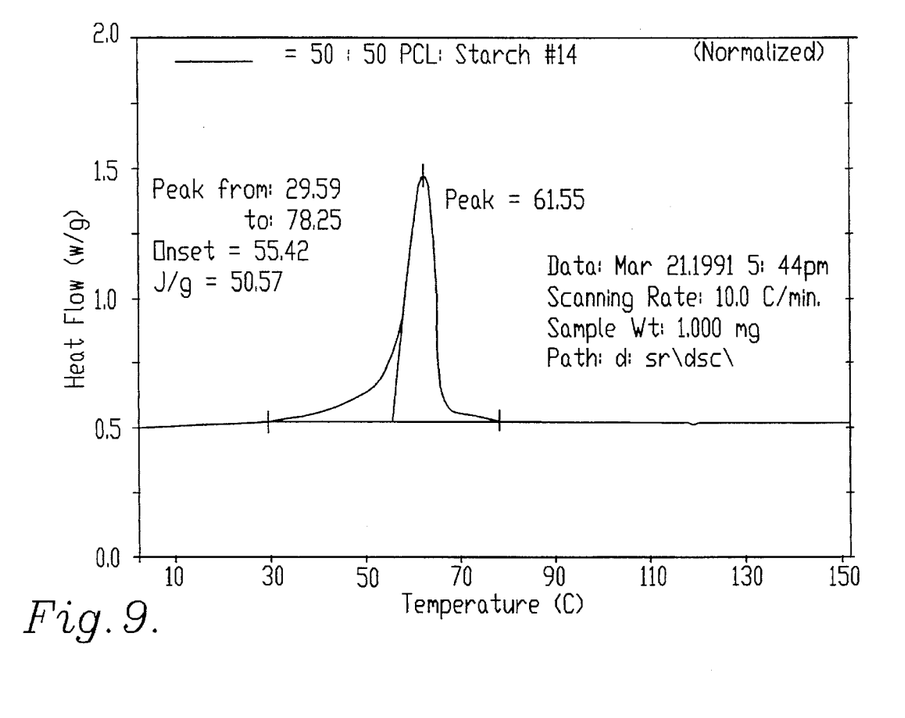
FIG. 9 is a DSC scan for a 50—50 starch-PCL blend after seventy minutes of mixing.
Figure 10:
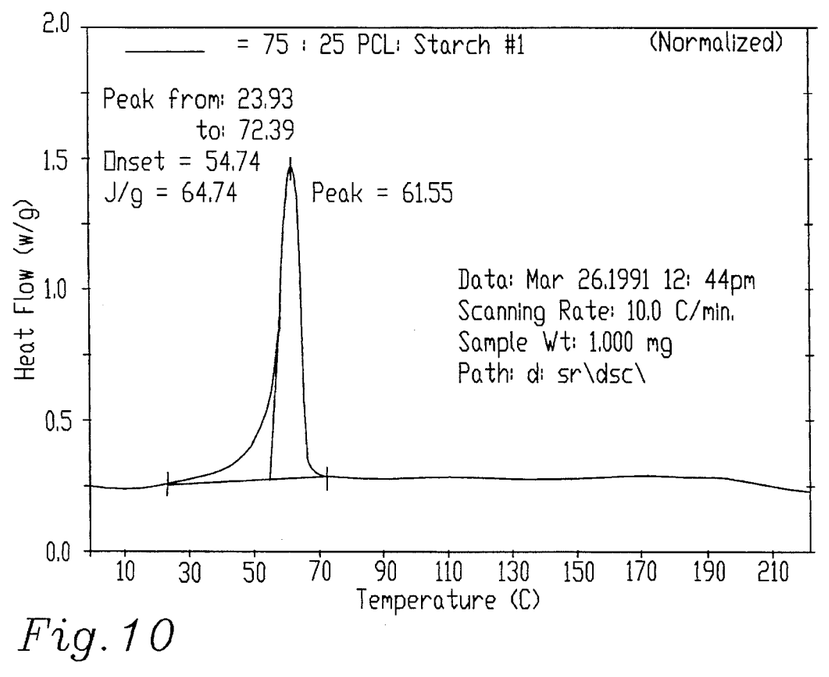
FIG. 10 after five minutes of mixing.
Figure 11:
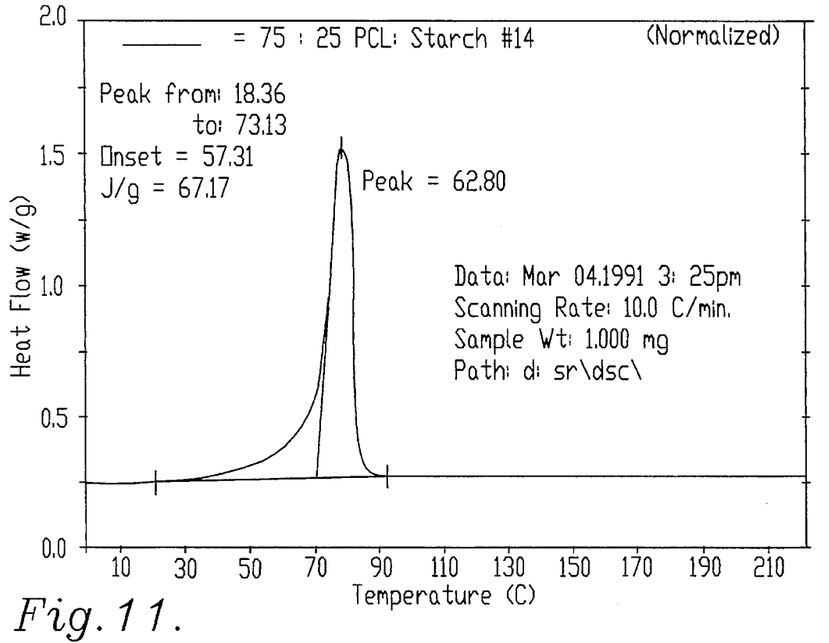
FIG. 11 is a DSC scan for a 25–75 starch PCL blend after seventy minutes of mixing.

Example 4—(Differential Scanning Calorimetry to Determine Extent of Change in Physical Properties of the Compositions Samples were drawn from the Brabender mixer when the starch-polymer compositions were being made, as previously described. The samples were drawn at different times to characterize the new blends formed in terms of their melt temperature and their heat of fusion. In addition, the effect, if any, of mixing time and the starch-PCL ratio on the thermal characteristics of the blend was ascertained. Ten samples for the case of 50—50 starch-PCL ratio and thirteen samples for the case where the starch to polymer ratio was 25–75 were drawn. Some of the thermograms are as shown in FIGS. 8 through 11. FIGS. 8 and 9 show DSC thermograms for 50—50 starch-PCL drawn after five minutes and after seventy minutes of blending. FIGS. 10 and 11 show DSC thermograms for 25–75 starch-PCL blends after 5 minutes and 70 minutes of mixing, respectively. Complete results are as presented in Tables 5 and 6. It can be observed from these thermograms that no change in the physical properties of the blend occurs even at extended times of mixing. In particular, the data developed in this example, when considered together with a visual and microscopic inspection, demonstrate that there is no evidence of chemical crosslinking or starch gelatinization.

TABLE 5

| Sample Number | Mixing time in minutes | Melting Temp, °C. | Heat of fusion (J/gm) | Percentage Crystallinity with respect to neat PCL |
|---|---|---|---|---|
| 1 | 5 | 58.74 | 87.02 | 62.38 |
| 2 | 10 | 54.72 | 69.76 | 50.01 |
| 3 | 20 | 56.26 | 91.48 | 65.58 |
| 4 | 25 | 58.08 | 87.22 | 62.52 |
| 5 | 35 | 54.48 | 68.10 | 48.82 |
| 6 | 45 | 58.58 | 87.40 | 62.65 |
| 7 | 50 | 54.50 | 71.06 | 50.94 |
| 8 | 60 | 56.49 | 91.08 | 65.29 |
| 9 | 65 | 55.62 | 101.12 | 72.49 |
| 10 | 70 | 55.42 | 101.14 | 72.50 |

TABLE 6

| Sample Number | Mixing time in minutes | Melting Temp, °C. | Heat of fusion (J/gm) | Percentage Crystallinity with respect to neat PCL |
|---|---|---|---|---|
| 1 | 5 | 54.74 | 90.32 | 64.75 |
| 2 | 10 | 55.86 | 79.47 | 56.97 |
| 3 | 15 | 55.33 | 87.06 | 62.41 |
| 4 | 20 | 55.34 | 86.61 | 62.09 |
| 5 | 30 | 56.22 | 86.68 | 62.14 |
| 6 | 35 | 56.39 | 84.68 | 60.70 |
| 7 | 40 | 55.98 | 85.24 | 61.10 |
| 8 | 45 | 56.31 | 84.24 | 60.39 |
| 9 | 50 | 56.23 | 186.83 | 62.24 |
| 10 | 55 | 56.04 | 186.05 | 61.68 |
| 11 | 60 | 55.55 | 83.95 | 60.81 |
| 12 | 65 | 55.19 | 88.32 | 63.31 |
| 13 | 70 | 57.31 | 90.28 | 64.72 |

Figure 12:
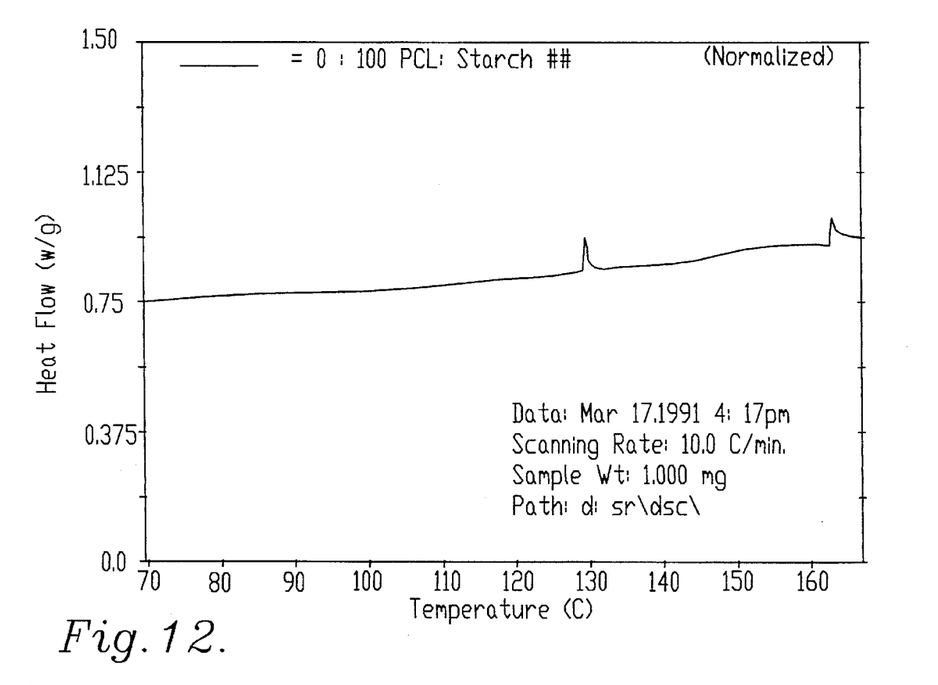
FIG. 12 is a DSC scan for neat (pure starch without other polymer) starch.
Figure 13:
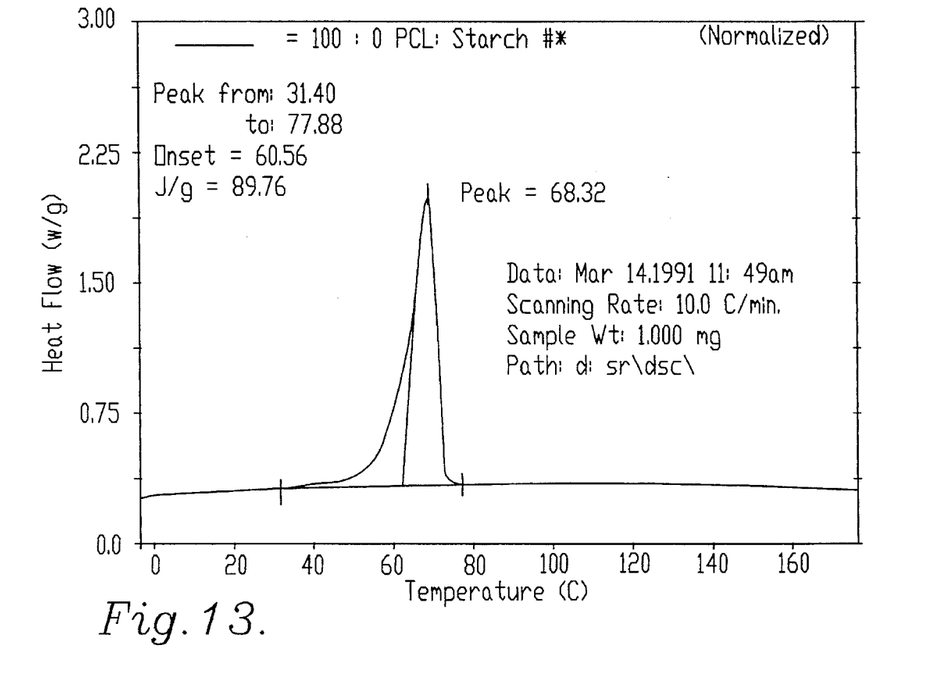
FIG. 13 is a DSC scan for neat PCL.

For pure starch, no thermal events were found to occur in the temperature range from 70° C. to 160° C. The DSC thermogram for pure starch is as shown in FIG. 12. The only two spikes that can be seen in this thermogram can be attributed to some artifacts of the instrument and cannot be explained in terms of any thermal event such as melting or glass transition of the polymer (starch). For neat PCL as shown in FIG. 13, melting of the sample occurred at 60.56° C. which compares well with the reported value of 63° C., for PCL of molecular weight 40,000. A value of 89.76 J/g was calculated for neat polycaprolactone. Comparison of this value with a value of 139.5 J/g reported for 100% crystalline polycaprolactone yields a percentage crystallinity of 64.34% for the PCL used in the examples. For a 50—50 blend of starch-PCL an average melting temperature of 56.28° C. and an average heat of fusion of 89.52 J/g was calculated. Similarly, for a 25–75 blend an average melting temperature of 55.91° C. and an average heat fusion of 85.76 Joule/gram was calculated. An average percentage crystallinity of 99.73% and 95.54% was calculated for the 50—50 and 25–75 Starch-PCL blends respectively with respect to the polycaprolactone used for this study. Thus, the addition of starch (an amorphous substance) does not seem to drastically change the crystallinity of the blend as compared to the polycaprolactone that was used in the examples. However, there is a melting point depression that is noticed in the case of starch-PCL blends as compared to neat PCL. This is probably due to some impurity in the starch dissolving in the molten PCL while blending.

Figure 14:
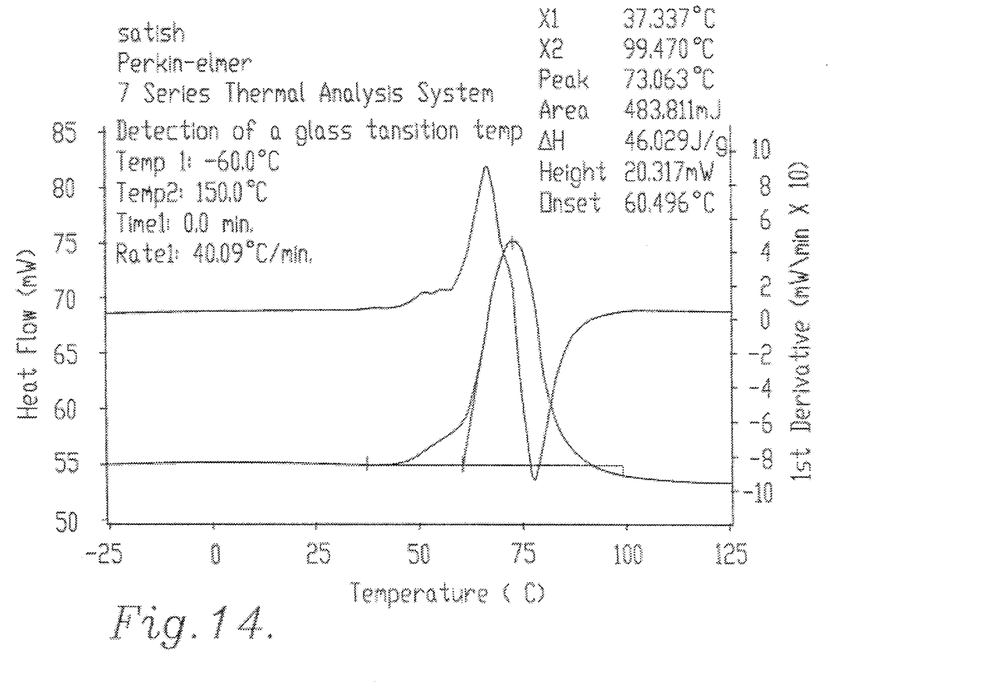
FIG. 14 is a portion of a DSC scan that was run on a temperature range from −60° C. to 150° C. on a 50—50 starch-PCL blend.

To determine whether any solubilization of starch in the PCL occurred, a DSC scan was run from a temperature of −60° C. to 150° C. This thermogram has been shown in FIG. 14. As no secondary transitions were observed in the low temperature range (before melting occurred), it could be inferred that the starch and PCL do not solubilize in one another and exist in the blend as two separate entities that are well-mixed.

Figure 15:
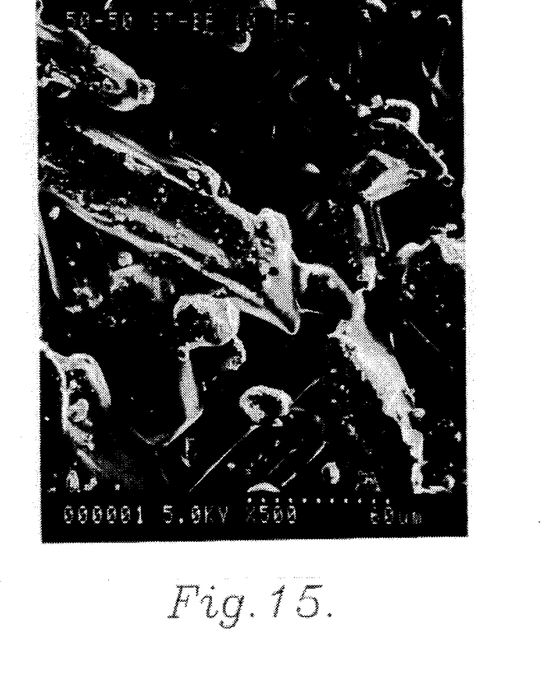
FIG. 15 is a scanning electron microscope photograph of a 50—50 starch-polycaprolactone slab.

FIG. 15 shows the surfaces of two 50—50 starch-polycaprolactone slabs as viewed under a scanning electron microscope (magnified 500 times). The starch granules are generally designated by the numeral 10 and polycaprolactone by the numeral 20. As is evident from FIG. 15, at least a portion of the starch granules are coated by the polycaprolactone, which coating operates to limit the rate of degradation of the starch when exposed to the environment.

Example 5 (Formulation Release Tests)

Example 5 is a laboratory test demonstrating that the release rates of malathion from the polymer/starch compositions of the instant invention are substantially lower than unencapsulated malathion.

Example 5 presents data from experiments which simulated grain storage conditions. The release experiments were carried out on cleaned, hard winter wheat with a moisture content of 15% by weight. Because malathion degradation processes are accelerated by contact with water, the high moisture content represented a "worst case" scenario. The release experiments were carried out using the following composition: (1) a 75:25 starch:PEG blend with 0.2 wt. % malathion; (2) a 90:10 starch:PEG blend with 0.1 wt. % malathion. The weight percents of malathion were selected so as to provide minimum chemical levels necessary for control against insect infestation.

1 kilogram of wheat was used for each composition. 10 grams of each formulation was mixed with the above wheat. This created a malathion level of (1) 20 ppm (parts per million; (2) 20 ppm and (3) 10 ppm for each of the above three formulations, respectively. The recommended level for insect control on wheat is 8 ppm. The mixing was done to distribute the formulation as a fine coating on the wheat. The treated wheat was then divided into two samples of 500 gm each, each forming a duplicate for malathion residue analysis. The samples were stored in sealed glass jars which were kept in the dark for the duration of the experiment. The experiment was carried out for 40 days.

The malathion content in the wheat was measured using High Performance Liquid Chromatography (HPLC) analysis. The technique for extraction and analysis of malathion from wheat was developed in this laboratory, and gives accurate results to a minimum level of 1 ppm. The wheat samples were withdrawn from the jars and were analyzed every 4 days.

Table 7 shows data comparing the malathion levels from composition 3(10 ppm) with malathion levels observed on 15 wt. % moisture wheat from the literature (Kadoum, A. M., and LaHue, D. W., "Degradation of Malathion in Corn, Wheat, and Sorghum Grain of High Moisture Content" *Journal of Economic Entomology*, 69, 205–206 (1976).

TABLE 7

| Days after Application | Malathion level from formulation (ppm) | Malathion level (Unencapsulated) (ppm) |
|---|---|---|
| 1 | 9.4 | 8.5 |
| 4 | 8.9 | 6.6 |
| 8 | 9.2 | 55.7 |
| 12 | 9.5 | 5.2 |
| 21 | 7.1 | 4.1 |

The data of Table 7 show that, when the composition of the invention is used, the effective malathion level on wheat can be maintained for a longer time period than can be done with unencapsulated malathion.

Figure 16:
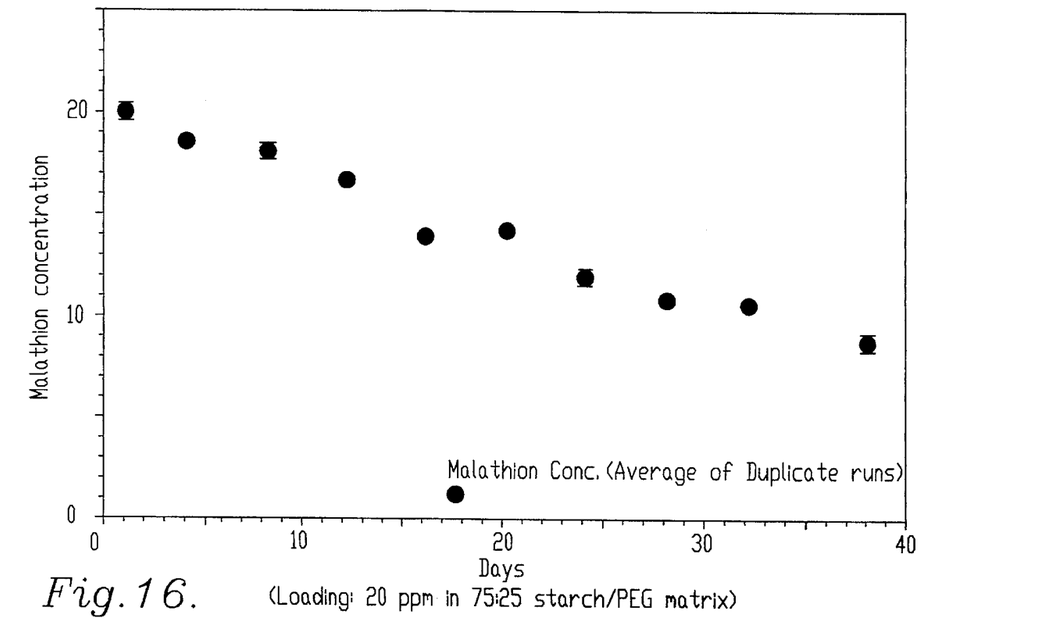
FIG. 16 is a plot showing the malathion level on wheat for 20 ppm malathion in a 75:25 starch/PEG composition.
Figure 17:
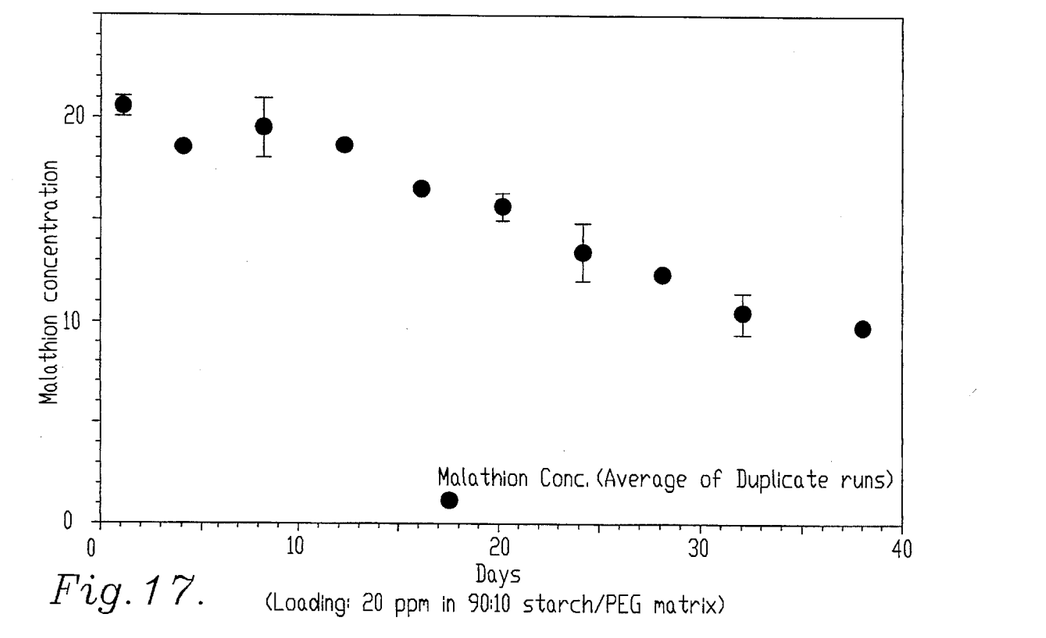
FIG. 17 is a plot showing the malathion level on wheat for 20 ppm malathion in a 90:10 starch/PEG composition.

FIGS. 15, 16 and 17 show the malathion level on wheat for the three compositions. The data points represent the average of duplicate runs and the error bars denote the standard deviation between the points for a given set.

Figure 18:
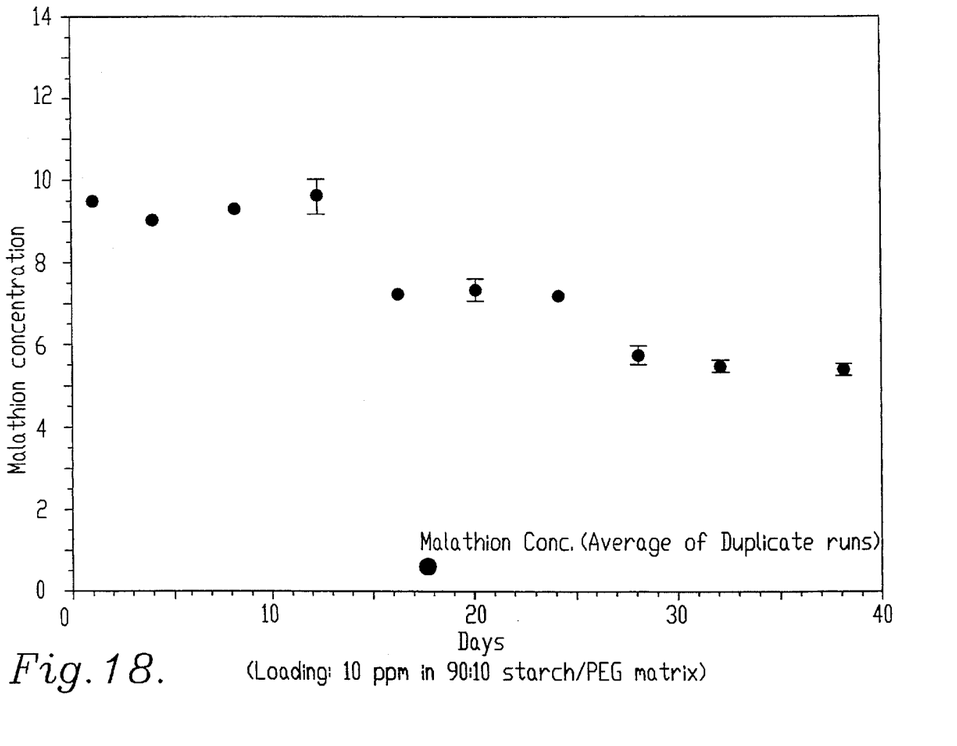
FIG. 18 is a plot showing the malathion level on wheat for 10 ppm malathion in a 90:10 starch/PEG composition.

FIG. 18 shows the comparison of malathion levels from the compositions 1 and 2. As can be seen from the figure, the formulation having the composition 90:10 starch:PEG retains malathion slightly better than the composition 75:25 starch:PEG.

Figure 19:
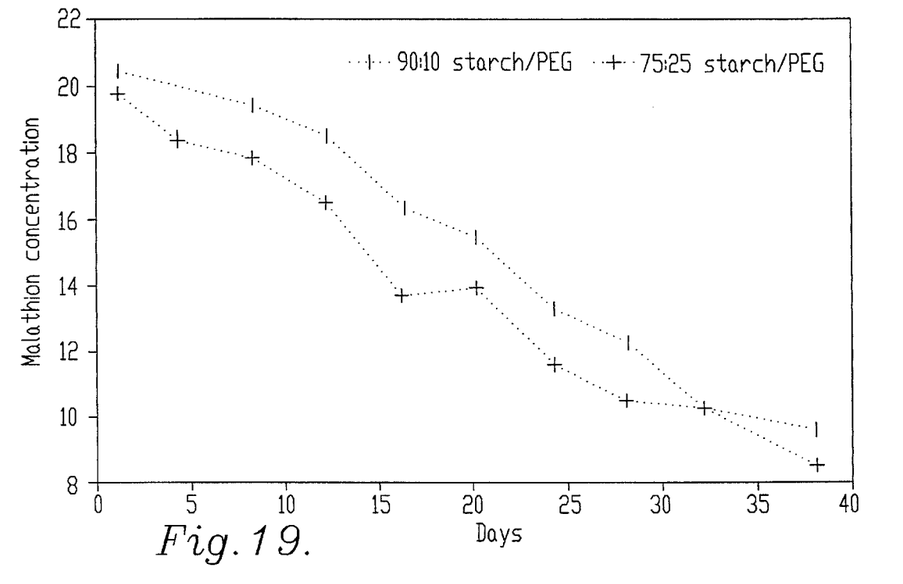
FIG. 19 is a plot showing the comparison of malathion levels from data shown in FIGS. 16 and 17.
Figure 20:
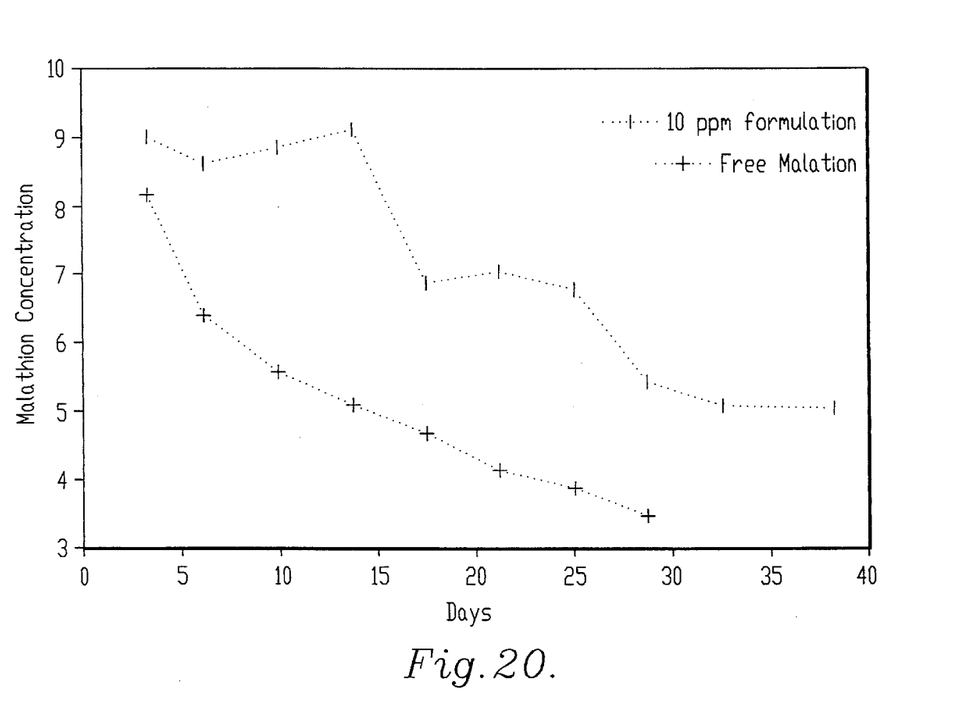
FIG. 20 shows a comparison of a 10% ppm malathion formulation of the instant invention and the release rate reported in the literature.

FIG. 19 shows the comparison of the malathion levels obtained from the invention and the unencapsulated malathion (Kadoum, A. M., and LaHue, D. W. as above). It can be observed that the invention provides sustained release of malathion for a longer period of time as compared to the unencapsulated malathion.

In the above-noted examples, it was discovered that coating granules of native, undenatured, ungelatinized starch with synthetic biodegradable polymers will effectively encapsulate the agent or active ingredient within a starch matrix without the use of chemical crosslinking agents. The resulting composition is a slow release composition particularly adapted for agricultural uses, but is also adapted for any use requiring a slow release of an active ingredient from a matrix, which matrix may be exposed to biological or aerobic attack.

All references are incorporated by reference.

I claim:

1. A slow release composition comprising a quantity of active ingredient interspersed within a release-extending admixture for slowing the release of said ingredient from said admixture, said admixture consisting essentially of a matrix comprising respective quantities of native, undenatured starch and synthetic polymer selected from the group consisting of poly caprolactone and polyethylene glycol, and combinations thereof, said polymer coating at least a portion of the surface area of said starch with said active ingredient interspersed within said matrix.

2. The composition of claim 1, said matrix comprising from about 25 to 75% by weight, non-active portion, starch, and from about 25 to 75% by weight, nonactive portion, synthetic polymer.

3. The composition of claim 2, said starch content from about 50 to 65% by weight of said matrix and said polymer content being from about 35 to 50% by weight of said matrix.

4. The composition of claim 1, said starch being selected from the group of starches derived from starches employing about 70 wt. % amylose and about 30 wt. % amylopectin.

5. The composition of claim 1, said synthetic polymer being selected from the group consisting of biodegradable polyesters accepted as safe for human consumption.

6. The composition of claim 1, said active ingredient being selected from the group consisting of biocides and therapeutic agents.

7. The composition of claim 6, said active ingredient being herbicide.

8. The composition of claim 1, said active ingredient being present at a level of from about 1 to 40% by weight.

9. A method of applying an active ingredient onto a desired area, said method comprising the step of applying to said area the slow-release composition of claim 1.

10. A slow release composition comprising a quantity of active ingredient interspersed within a release-extending admixture for slowing the release of said ingredient from said admixture, said admixture in the form of a matrix comprising respective quantities of native, undenatured starch and synthetic polymer, said polymer coating at least a portion of the surface area of said starch with said active ingredient interspersed within said matrix, said starch being less than 2 wt. % gelatinized and said composition being in the form of a particulated flowable material.

11. The composition of claim 10, said matrix comprising from about 25 to 75% by weight, non-active portion, starch, and from about 25 to 75% by weight, non-active portion, synthetic polymer.

12. The composition of claim 11, said starch content from about 50 to 65% by weight of said matrix and said polymer content being from about 35 to 50% by weight of said matrix.

13. The composition of claim 10, said starch being selected from the group of starches derived from starches employing about 70 wt. % amylose and about 30 wt. % amylopectin.

14. The composition of claim 10, said synthetic polymer being selected from the group consisting of biodegradable polyesters accepted as safe for human consumption.

15. The composition of claim 10, said active ingredient being selected from the group consisting of biocides and therapeutic agents.

16. The composition of claim 15, said active ingredient being herbicide.

17. The composition of claim 10, said active ingredient being present at a level of from about 1 to 40% by weight.

18. A method of applying an active ingredient onto a desired area, said method comprising the step of applying to said area the slow-release composition of claim 10.

* * * * *